United States Patent
Meyrueix et al.

(10) Patent No.: US 10,052,289 B2
(45) Date of Patent: Aug. 21, 2018

(54) COMPOSITION COMPRISING AN ACTIVE AGENT WITH LOW AQUEOUS SOLUBILITY

(75) Inventors: Rémi Meyrueix, Lyons (FR); Rafael Jorda, Merignac (FR); Gauthier Pouliquen, Lyons (FR); You-Ping Chan, Ternay (FR); Olivier Breyne, Lyons (FR)

(73) Assignee: Flamel Ireland Limited, Dublin (IE)

( * ) Notice: Subject to any disclaimer, the term of this patent is extended or adjusted under 35 U.S.C. 154(b) by 867 days.

(21) Appl. No.: 12/641,773

(22) Filed: Dec. 18, 2009

(65) Prior Publication Data
US 2010/0178337 A1 Jul. 15, 2010

Related U.S. Application Data

(60) Provisional application No. 61/141,834, filed on Dec. 31, 2008, provisional application No. 61/145,271, filed on Jan. 16, 2009.

(30) Foreign Application Priority Data

Dec. 31, 2008 (FR) ..................................... 08 59170
Dec. 18, 2009 (WO) ................. PCT/FR2009/052613

(51) Int. Cl.
| | | |
|---|---|---|
| A61K 9/52 | (2006.01) | |
| A61K 9/14 | (2006.01) | |
| A61K 9/22 | (2006.01) | |
| A61K 31/337 | (2006.01) | |
| A61K 31/403 | (2006.01) | |
| A61K 31/366 | (2006.01) | |
| A61K 31/4418 | (2006.01) | |
| A61K 31/496 | (2006.01) | |
| A61K 38/13 | (2006.01) | |
| A61P 35/00 | (2006.01) | |
| A61P 37/00 | (2006.01) | |
| A61P 31/10 | (2006.01) | |
| A61P 9/12 | (2006.01) | |
| A61P 3/06 | (2006.01) | |
| A61K 9/50 | (2006.01) | |
| A61K 9/51 | (2006.01) | |
| A61K 47/34 | (2017.01) | |

(52) U.S. Cl.
CPC .......... *A61K 9/5078* (2013.01); *A61K 9/5146* (2013.01); *A61K 9/5015* (2013.01); *A61K 9/5026* (2013.01); *A61K 47/34* (2013.01)

(58) Field of Classification Search
CPC .... A61K 9/5078; A61K 9/5146; A61K 47/34; A61K 9/5015; A61K 9/5026
See application file for complete search history.

(56) References Cited

U.S. PATENT DOCUMENTS

| | | | |
|---|---|---|---|
| 5,904,936 A | 5/1999 | Huille et al. | |
| 6,630,171 B1 | 10/2003 | Huille et al. | |
| 7,683,024 B2 | 3/2010 | Chan et al. | |
| 8,293,255 B2 | 10/2012 | Soula et al. | |
| 2005/0037077 A1 | 2/2005 | Legrand et al. | |
| 2006/0099264 A1* | 5/2006 | Chan et al. | ................... 424/486 |
| 2007/0010652 A1 | 1/2007 | Angot et al. | |
| 2007/0196497 A1 | 8/2007 | Pouliquen et al. | |
| 2009/0012028 A1 | 1/2009 | Chan et al. | |
| 2009/0220611 A1 | 9/2009 | Dargelas et al. | |

FOREIGN PATENT DOCUMENTS

| | | |
|---|---|---|
| FR | 2 840 614 | 12/2003 |
| FR | 2 855 521 | 12/2004 |
| WO | WO 96/29991 | 10/1996 |
| WO | WO 03/030878 | 4/2003 |
| WO | WO 03/104303 | 12/2003 |
| WO | WO 2005/051416 | 6/2005 |
| WO | 2008/025425 A1 | 3/2008 |
| WO | WO 08/135563 | 11/2008 |
| WO | 2010/012940 A2 | 2/2010 |
| WO | 2010/076519 A1 | 7/2010 |

OTHER PUBLICATIONS

International Preliminary Report on Patentability—English Translation—WO 2010/076519 (PCT/FR2009/052613) dated Jul. 5, 2011 (Jul. 5, 2011); 12 pgs.
CN 200980156523, English translation of First Office Action dated Aug. 28, 2012; 7 pgs.
CN 200980156523, English translation of Second Office Action dated Jun. 9, 2013; 5 pgs.
CN 201410055819, English translation of First Office Action dated Dec. 22, 2014; 5 pgs.
CN 201410055819, English translation of Second Office Action dated Nov. 9, 2015; 5 pgs.
EP 09805748, Office Action dated May 30, 2013; 4 pgs.
EP 09805748, Office Action dated Mar. 29, 2017; 4 pgs.
JP 2011544070, English translation of Office Action dated Jun. 12, 2013; 4 pgs.

\* cited by examiner

*Primary Examiner* — Matthew P Coughlin
*Assistant Examiner* — Thurman Wheeler

(57) ABSTRACT

The present invention relates to a composition comprising at least one active ingredient with low aqueous solubility, said active ingredient being present therein in a form noncovalently associated with nanoparticles formed by at least one POM polymer of formula (I), and in which said active ingredient is present in a proportion of at least 5 μmol/g of POM.
It is also directed towards the use of such nanoparticles, noncovalently associated with an active ingredient, with a view to increasing the aqueous solubilization of said active ingredient.

38 Claims, No Drawings

COMPOSITION COMPRISING AN ACTIVE AGENT WITH LOW AQUEOUS SOLUBILITY

The present invention aims to propose compositions suitable for the formulation of active ingredient(s), abbreviated to "AI", in particular with low aqueous solubility. It also aims to propose an effective method of formulation for, in general, increasing the aqueous solubilization of any active ingredient.

As described hereinafter, a large number of active ingredients, whether they are therapeutic, prophylactic or cosmetic, can pose problems in terms of formulation from the viewpoint of an aqueous solubility that is considered to be insufficient.

In particular, it is found to be very difficult to formulate active ingredients which have a low water-solubility, in a form compatible with oral administration, a route particularly favoured for the administration of active ingredients, in particular from the viewpoint of the patient comfort thereof and the compatibility thereof with a large variety of formulations.

Thus, the oral bioavailability of active ingredients of class 2 or 4 of the biopharmaceutical classification is for the most part limited by their low solubility. In particular, paclitaxel, a natural taxoid, which is widely used for the treatment of tumours, is representative of these relatively non-water-soluble active ingredients. The very low aqueous solubility of this compound, which is less than 1 µg/ml, makes it difficult to formulate the latter.

In this context, the development of additives for increasing the aqueous solubility of active ingredients is of considerable interest.

Ideally, a solubilization additive should have several essential characteristics.

First of all, it should, for obvious reasons, have a high solubilizing power. Thus, it is necessary for the polymer to solubilize a sufficiently large amount of AI. This has two advantages. This ability makes it possible to minimize the amount of additive, which may be essential for tolerance in the case of a parenteral form. Moreover, a high solubility makes it possible to render the unit dose readily administrable to the patient, whether orally or parenterally.

Moreover, the solubilization additive as such, as well as the formulation protocol selected for combining it with the active ingredient considered, should not degrade the active ingredient. Thus, it is a determining factor that the various steps of the formulation of the active ingredient and of the solubilization additive do not result in a partial degradation of the active ingredient. A potential degradation could occur, for example, during an increase in temperature, by using surfactants, by bringing the active ingredient into contact with an organic solvent, or a high shear stress. Now, certain active ingredients, in particular peptides and proteins, are particularly sensitive to these methods of degradation. It is therefore particularly important that the solubilization additive could be used in an aqueous process which does not require an excessive temperature, any surfactant, or any organic solvent.

Furthermore, it is advantageous for the formulation of the active ingredient with a solubilization additive to have a low viscosity. Thus, for an active ingredient intended for parenteral administration, the viscosity of the suspension containing the active ingredient and the solubilizing agent should be sufficiently low to allow easy injection through a needle of small diameter, for example a needle of gauge 27 to 31. In fact, even in the case of oral administration of an AI contained in a tablet, a low viscosity of the suspension solubilizing the active ingredient remains a decisive advantage for the steps of manufacturing microparticles, tablets or any other pharmaceutical form known to those skilled in the art. This low-viscosity requirement is particularly restrictive since it limits the acceptable amount of solubilizing additive and excludes the use of high-molecular-mass polymer-type additives which are highly water-soluble but have high viscosities.

Finally, in the perspective of parenteral administration, it is desirable for the solubilizing additive to be completely tolerated and to degrade rapidly, i.e. over a timescale of a few days to a few weeks. It is also preferable for the amount of this additive to be as limited as possible.

The development of a solubilization additive which makes it possible to solubilize active ingredients at a sufficiently high concentration and which simultaneously meets all the requirements summarized above is tricky and, to the inventor's knowledge, has not been achieved to date.

Several alternatives have already been proposed for attempting to compensate for the deficiency in bioavailability of weakly water-soluble active ingredients. Among these, a particularly advantageous alternative uses micellar solutions. Polymeric micelles formed from amphiphilic copolymers, for example from PLGA-PEG diblock copolymers, are thus known. In this formulation method, the active ingredient is solubilized within the hydrophobic PLGA core of the micelles.

However, this approach has in particular two limitations: firstly, a moderately soluble AI, for instance a peptide with medium solubility, may be difficult to solubilize in the hydrophobic core and, secondly, the method of producing the nanoparticles comprises a step of solubilizing the PLGA in a hydrophobic solvent, which step should be avoided for certain fragile AIs.

The present invention precisely aims to propose new compositions which are particularly advantageous from the viewpoint of active ingredients with low aqueous solubility, in so far as they make it possible to meet all the abovementioned requirements.

According to a first of its aspects, the present invention thus relates to a composition comprising at least one active ingredient with low aqueous solubility, in particular less than 1 g/l of pure water, said active ingredient being present therein in a form noncovalently associated with nanoparticles formed by at least one POM polymer of formula (I) defined below or one of its pharmaceutically acceptable salts and in which said active ingredient is present in a proportion of at least 5 µmol/g of POM polymer.

According to another of its aspects, the invention relates to a composition comprising at least one active ingredient with medium aqueous solubility, in particular comprised between 1 g/l and 30 g/l of pure water, said active ingredient being present therein in a form associated noncovalently with nanoparticles formed by at least one POM polymer of formula (I) defined below or one of its pharmaceutically acceptable salts and in which said active ingredient is present in a proportion of at least 5 µmol/g of POM polymer.

According to another of its aspects, the invention also relates to the use of nanoparticles, as defined above, of at least one POM polymer, noncovalently associated with an active ingredient, with a view to increasing the aqueous solubilization of said active ingredient.

Advantageously, a composition of the invention makes it possible to solubilize the active ingredients considered in a stable, low-viscosity liquid form which can be readily handled and/or injected through needles of small diameter. It also has the advantage of being biocompatible and of not requiring, in order to be used, a step of denaturing formulation, or use of an organic solvent or surfactants.

Admittedly, polymer nanoparticles have already been proposed as a method for parenteral administration of various active ingredients. Nanoparticles of a copolyamino acid comprising hydrophobic groups and hydrophilic groups are thus proposed in documents WO 96/29991 and WO 03/104303 from the company Flamel Technologies. Document WO 03/104303 discloses more particularly a polymer of polyamino acid type comprising aspartic residues and/or glutamic residues, with at least a part of these residues comprising at least one alpha-tocopherol unit. These "hydrophobically modified" homopolyamino acids spontaneously form, in water, a colloidal suspension of nanoparticles, which are capable of readily associating in an aqueous suspension at pH 7.4, with at least one active protein. As for application WO 2005/051416, it proposes biodegradable polyamino acids which can be transformed into colloidal vectorization nano- or microparticles capable of reversibly associating with active ingredients and of providing sustained release of said active ingredients.

However, these documents are in no way concerned with the problem of lack of aqueous solubility posed by certain active ingredients. What is more, the teaching therein is not capable of guiding those skilled in the art towards the choice of a specific structure of polymer for solving this problem.

Thus, the present invention results in particular from the discovery by the inventors that the solubilizing power of specific amphiphilic polymers bearing hydrophobic groups, in particular those of the family of polyglutamates bearing pendent vitamin E units, depends singularly on the degree of substitution with hydrophobic groups. More specifically, the inventors have noted that the solubilizing power is not proportional to the amount of hydrophobic groups borne by the polymer. The solubilizing power first of all increases rapidly with the amount of hydrophobic groups, and then reaches a plateau, or even goes through a maximum and then decreases slowly. Without wishing to be limited by the theory, it may be assumed that the solubilizing power results from a compromise between, firstly, the abundance of hydrophobic groups and, secondly, the accessibility thereof.

As indicated above, the solubilizing power is not the only parameter to be taken into account for enabling optimal administration. The inventors have thus also noted that, in order to reduce the viscosity of the suspension, it is advisable to increase the proportion of hydrophobic groups and to favour low degrees of polymerization. Here again, without wishing to be bound by the theory, it may be assumed that small polymers that are highly substituted with hydrophobic groups self-associate into particles of greater density.

The inventors have thus discovered that it is possible to greatly improve the aqueous solubilization of active ingredients, in particular of active ingredients with low or medium water-solubility, so as to achieve a sufficient concentration of solubilized active ingredients, in order to enable in particular the administration thereof in a unit dose of acceptable size for the patient, this being through the use of nanoparticles of at least one POM polymer of formula (I) defined subsequently, having in particular a degree of polymerization comprised between 25 and 250, more particularly comprised between 40 and 100 and a grafting rate with hydrophobic groups ranging from 4 to 25 molar %, even 5 to 22 molar %.

Advantageously, the formulation considered according to the invention may also be capable of providing a release profile for this active ingredient that is regulated as a function of time.

In a preferred embodiment of the invention, the inventors have discovered that advantageously, the degree of polymerization of the polymer must be comprised between 25 and 100 and the grafting rate with hydrophobic groups comprised between 5 and 25%.

Without wishing to be limited by the theory, it seems that too low a degree of polymerization does not make it possible to easily control the number of grafts of hydrophobic groups per chain.

Conversely, too high a degree of polymerization, in particular strictly greater than 100, results in a colloidal suspension the viscosity of which becomes significant even for limited concentrations, which must be avoided for parenteral administration of the product.

As regards the grafting rate, to their credit, the inventors have discovered that such a rate, when it ranges from 5 to 25%, allows an optimum solubilizing power of the corresponding POM polymer to be reached.

Thus, the inventors have noted that a grafting rate that is too high, in particular strictly greater than 25%, even greater than 22%, results in nanoparticles of the POM polymer having a limited colloidal stability in the pH range comprised between 6.0 and 7.2, which is the pH range must frequently used for pharmaceutical forms.

Active Ingredients

As mentioned above, the present invention is directed towards solubilizing in sufficient concentrations, active ingredients with a low or medium aqueous solubility and/or increasing the aqueous solubilization of active ingredients in general.

The invention is thus found to be quite particularly advantageous with regard to weakly water-soluble active ingredients.

For the purpose of the present invention, an active ingredient with low aqueous solubility is a compound having a solubility of less than 1 g/l, in particular less than 0.1 g/l, in pure water, measured at ambient temperature, i.e. approximately 25° C.

For the purpose of the invention, a pure water is a water with a pH close to neutrality (between pH 5 and pH 8) and devoid of any other solubilizing compound known to those skilled in the art, such as surfactants or polymers (PVP, PEG).

The active ingredients considered according to the invention are advantageously biologically active compounds which can be administered to an animal or human organism.

According to one variant embodiment, these active ingredients are non-peptide active ingredients.

In general, an active ingredient according to the invention may be any molecule of therapeutic, cosmetic, prophylactic or imaging interest.

Advantageously, the active ingredients according to the invention are active ingredients of small size.

The term "active ingredients of small size" is intended to mean organic molecules having a mass of less than 2,000 Da, in particular less than 1,000 Da.

Thus, in the pharmaceutical field, the active ingredients with low aqueous solubility according to the invention may in particular be chosen from anticancer agents, antifungal agents, steroids, anti-inflammatories, sex hormones, immunosuppressants, antiviral agents, anaesthetics, antiemetics and antihistamines More particularly, as examples of specific active ingredients with low aqueous solubility, mention may be made of taxane derivatives such as paclitaxel, nifedipine, carvedilol, camptothecin, doxorubicin, cisplatin, 5-fluorouracil, cyclosporin A, PSC 833, amphotericin B, itraconazole, ketoconazole, betamethasone, indomethacin, testosterone, oestradiol, dexamethasone, prednisolone, triamcinolone acetonide, nystatin, diazepam, amiodarone, verapamil, simvastatin, rapamycin and etoposide.

According to one particular embodiment, the active ingredient considered according to the invention is an active ingredient of therapeutic interest.

According to another particular embodiment, the active ingredient may be chosen from paclitaxel, carvedilol base, simvastatin, nifedipine ketoconazole and cyclosporin A.

According to one embodiment of the invention, the active ingredient may be a molecule with medium aqueous solubility, the solubility of which can be increased by means of a composition according to the invention.

The expression "molecule with medium aqueous solubility" is intended to mean a molecule the solubility of which, in pure water, measured as indicated above, at ambient temperature, is comprised between 1 and 30 g/l, in particular comprised between 2 and 20 g/l of pure water.

By way of nonlimiting illustration of active ingredients according to the invention, the solubility of which can be increased, mention may in particular be made of:

proteins or glycoproteins, in particular interleukins, erythropoietin or cytokines, proteins bound to one or more polyalkylene glycol chains [preferably, polyethylene glycol (PEG): "PEGylated proteins"], peptides, polysaccharides, liposaccharides, oligonucleotides, polynucleotides, and mixtures thereof.

According to the present invention, the active ingredient is present in a composition of the invention in a proportion of at least 5 µmol/g of POM polymer, more particularly in a proportion of at least 10 µmol/g of POM, more particularly in a proportion of at least 20 µmol/g of POM, and even more particularly in a proportion of at least 100 µmol/g of POM.

Nanoparticles

The active ingredient, as described above, is present in a composition according to the invention at least in part in a form noncovalently associated with nanoparticles formed by at least one POM polymer of formula (I) below, or a pharmaceutically acceptable salt thereof:

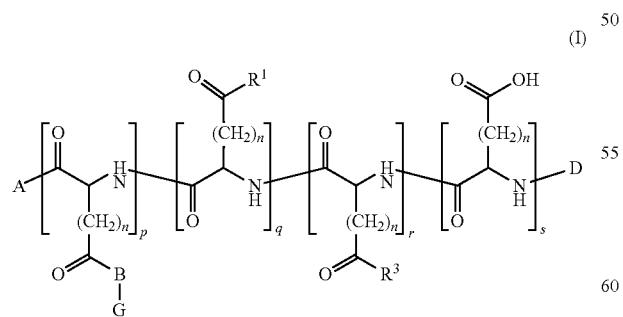

(I)

in which:

A represents:

RNH— in which R represents an H, a linear $C_2$ to $C_{10}$ alkyl, a branched $C_3$ to $C_{10}$ alkyl or a benzyl, or a terminal amino acid residue of formula:

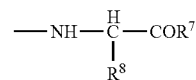

in which:
—$R^7$ is —OH, —$OR^9$ or —$NHR^{10}$, and
—$R^8$, —$R^9$ and —$R^{10}$ independently represent an H, a linear $C_2$ to $C_{10}$ alkyl, a branched $C_3$ to $C_{10}$ alkyl or a benzyl;

B is a direct bond, or a divalent, trivalent or tetravalent linking group, preferably chosen from the following radicals:
—O—, —NH—, —N($C_{1-5}$ alkyl)-, or an amino acid residue, diol residue, triol residue, diamine residue, triamine residue, aminoalcohol residue or hydroxy acid residue containing from 1 to 6 carbon atoms;

D represents an H, a linear $C_2$ to $C_{10}$ acyl, a branched $C_3$ to $C_{10}$ acyl or a pyroglutamate;

the hydrophobic groups G each represent, independently of one another, a radical chosen from:
linear or branched $C_8$ to $C_{30}$ alkyls which may optionally comprise at least one unsaturation and/or at least one heteroatom (preferably O and/or N and/or S), or
$C_8$ to $C_{30}$ alkylaryls or arylalkyls which may optionally comprise at least one unsaturation and/or at least one heteroatom (preferably O and/or N and/or S), or
$C_8$ to $C_{30}$ (poly)cyclics which may optionally comprise at least one unsaturation and/or at least one heteroatom (preferably O and/or N and/or S);
and preferably a radical chosen from the following group: octyloxy-, dodecyloxy-, tetradecyloxy-, hexadecyloxy-, octadecyloxy-, 9-octadecenyloxy-, tocopheryloxy- or cholesteryloxy-, B then being a direct bond;

$R^1$ represents a radical chosen from the group having the following formulae:
—NH—$(CH_2)_w$—$NH_3^+$, $Z^-$ with w comprised between 2 and 6, and preferably w is equal to 4,
—NH—$(CH_2)_4$—NH—C(=NH)—$NH_3^+$, $Z^-$,
—O—$(CH_2)_2$—$NH_3^+$, $Z^-$,
—O—$(CH_2)_2$—$N^+(CH_3)_3$, $Z^-$,
an amino acid residue or
a compound of formula:

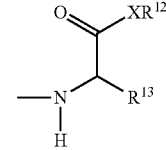

in which:
X is an oxygen atom or a —NH—,
$R^{12}$ is an —H, a linear $C_2$ to $C_{10}$ alkyl, a branched $C_3$ to $C_{10}$ alkyl or a benzyl,
—$R^{13}$ is —$(CH_2)_4$—$NH_3^+$, $Z^-$, —$(CH_2)_3$—NH—C(=NH)—$NH_3^+$, $Z^-$, or —$(CH_2)_3$—$NH_3^+$, $Z^-$;

in which:
the counteranion $Z^-$ is a chloride, a sulphate, a phosphate or an acetate, preferably a chloride;

$R^3$ represents a hydroxyethylamino-, a dihydroxypropylamino, an alkylene glycol residue, a polyoxyalkylene glycol or a radical of formula:

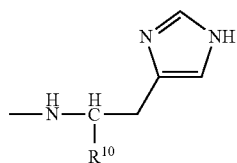

where $-R^{10}$ represents $-H$, $-CO_2H$, an alkyl ester (preferably $-COOMe$ or $-COOEt$), $-CH_2OH$, $-C(=O)-NH_2$, $-C(=O)-NH-CH_3$, or $-C(=O)-N(CH_3)_2$;

n is 1 or 2;

p, q, r and s are positive integers with it being possible for q, r and s to additionally be zero;

(p+q+r+s) ranges from 25 to 250, in particular from 40 to 250, more particularly from 40 to 150, and preferably from 50 to 100;

the molar grafting rate of the hydrophobic groups G, (p)/(p+q+r+s), ranges from 4 to 25 molar %, in particular from 5 to 22 molar %, preferably from 10 to 21 molar %;

the overall degree of charge of the chain $Q=(q-s)/(p+q+r+s)$ may be positive or negative;

it being possible for the series of the monomers of said general formula I to be random, of monoblock or multiblock type.

According to a particularly preferred embodiment, the POM polymer considered according to the invention is a POM polymer of formula (I) above, in which (p+q+r+s) ranges from 25 to 100, and the molar grafting rate with hydrophobic groups G, (p)/(p+q+r+s) ranges from 5 to 25% molar.

Such polymers are in particular described in detail in document WO 2008/135563, the content of which is incorporated by way of reference. For further details on the synthesis of said polymers, it will be useful to refer to documents FR 2 840 614 and FR 2 855 521.

Preferably, the hydrophobic groups are represented by a radical chosen from the following group: octyloxy-, dodecyloxy-, tetradecyloxy-, hexadecyloxy-, octadecyloxy-, 9-octadecenyloxy-, tocopheryloxy- or cholesteryloxy-, B then being a direct bond.

Quite particularly suitable for the invention are the compounds of general formula (I') corresponding to general formula I in which:

A represents $-NH_2$,

B is a direct bond,

D represents a hydrogen atom or a pyroglutamate, the hydrophobic groups each represent, independently of one another, a radical chosen from: octyloxy-, dodecyloxy-, tetradecyloxy-, hexadecyloxy-, octadecyloxy-, 9-octadecenyloxy-, tocopheryloxy- or cholesteryloxy-, and $R^3$ represents a hydroxyethylamino- or a dihydroxypropylamino Preferably, the hydrophobic groups G and the anionic groups and the cationic groups if present, are arranged randomly as pendant groups.

According to one embodiment of the invention, at least one and preferably all of the hydrophobic groups represent a tocopheryloxy radical.

The compounds of general formula I may be distinguished in particular according to the chemical nature of the hydrophobic groups that they respectively bear, and also as a function of the molar grafting rate with these hydrophobic groups.

Moreover, as regards their percentage of grafting with cationic and/or anionic groups, the compounds of general formula I may be anionic, neutral or cationic at neutral pH.

According to one variant embodiment, the compounds are represented by a general formula I in which:

(q)/(p+q+r+s) is less than 1%, and (r)/(p+q+r+s) is less than 1%.

According to a particularly advantageous embodiment, the POM polymer according to the invention is of formula (II) below, or a pharmaceutically acceptable salt thereof:

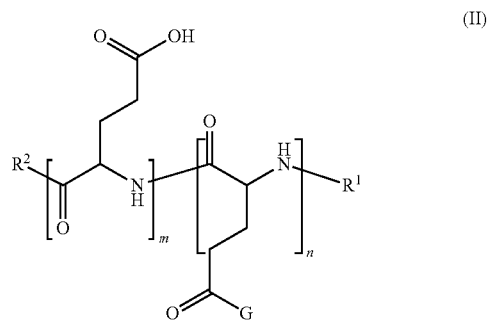

in which:

$R^1$ represents a hydrogen atom, a linear $C_2$ to $C_{10}$ acyl group, a branched $C_3$ to $C_{10}$ acyl group, a pyroglutamate group or a hydrophobic group G;

$-R^2$ represents a $-NHR^5$ group or a terminal amino acid residue linked by the nitrogen and the carboxyl of which is optionally substituted with an alkylamino radical $-NHR^5$ or an alkoxy $-OR^6$;

$R^5$ represents a hydrogen atom, a linear $C_1$ to $C_{10}$ alkyl group, a branched $C_3$ to $C_{10}$ alkyl group or a benzyl group;

$R^6$ represents a hydrogen atom, a linear $C_1$ to $C_{10}$ alkyl group, a branched $C_3$ to $C_{10}$ alkyl group, a benzyl group or a group G;

G represents a tocopheryloxy radical;

m and n are positive, non-zero integers;

(m+n) ranges from 25 to 250, in particular from 40 to 250, more particularly from 40 to 150, preferably from 50 to 100;

the molar grafting rate of the hydrophobic groups G, (n)/(n+m) ranges from 4 to 25 molar %, in particular from 5 to 22 molar %, preferably from 10 to 21%;

it being possible for the series of the monomers of said general formula II to be random, of monoblock or multiblock type, preferably being random.

According to one variant of the invention, polymers of formula I or II, the grafting rate of which ranges from 10 to 21 molar % and the DP of which is comprised between 50 and 150 are quite particularly suitable as POM polymers for the invention.

According to a particularly preferred embodiment, the POM polymer according to the invention is a polymer of formula I or II above, the grafting rate of which ranges from 5 to 25 molar %, even 5 to 22 molar %, and the DP of which is comprised between 25 and 100.

It may in particular be a polyglutamate having a degree of polymerization of approximately 100 and which is 15% or 20%-grafted with vitamin E.

The general formulae (I) and (II) described above should not be interpreted as representing only sequenced (or block) copolymers, but also random copolymers or multiblock copolymers.

The term "pharmaceutically acceptable salts" of the polymer according to the invention is intended to mean all the polymers with the counterions associated with the ionized functions of the polymer. For certain structures where there is coexistence of positive and negative charges, it is also possible to envisage total or partial neutralization of the charges.

The terms "association" or "associated" used to describe the relationships between one or more active ingredients and the POM polymer according to the invention mean that the active ingredient(s) is (are) associated with the POM polymer(s) via noncovalent physical interactions, in particular hydrophobic interactions, and/or electrostatic interactions and/or hydrogen bonds and/or via a steric encapsulation by the POM polymers.

This association is generally the result of hydrophobic and/or electrostatic interactions produced by the units of the POM polymer, in particular hydrophobic or ionized units, capable of generating this type of interaction.

The POM polymers considered according to the invention are in particular capable of spontaneously forming nanoparticles when said polymers are dispersed in an aqueous medium, and in particular water.

In general, the size of the nanoparticles ranges from 1 to 1,000 nm, in particular from 5 to 500 nm, especially from 10 to 300 nm, and more particularly from 10 to 100 nm.

The size of the POM nanoparticles is evaluated by the average hydrodynamic diameter of these particles. The measurement is carried out by quasi-elastic light scattering with an ALV CGS-3 apparatus. For this purpose, the POM suspension is concentrated at 0.5 mg/ml in a saline medium such as 0.15 M NaCl, after a standing time sufficient to reach equilibrium.

Advantageously, the POM polymer is biodegradable.

According to one particular embodiment, a POM polymer suitable for the invention may bear one or more grafts of polyalkylene glycol type linked to a glutamate unit constituting it. Preferably, the polyalkylene glycol is a polyethylene glycol and more particularly used with a molar percentage of polyethylene glycol grafting ranging from 1% to 30%.

It should also be noted that the residual carboxylic functions of the modified polyglutamate according to the invention are either neutral (COOH form) or ionized (COO$^-$ anion), according to the pH and the composition. Reference will therefore be made without distinction to i) glutamate residue or glutamic acid residue, ii) polyglutamic acid or a polyglutamate.

The coupling of the cationic and, optionally, neutral groups with an acid function of the POM polymer of formula (I) or (II) is carried out simultaneously in a second step in the presence of a chloroformate as coupling agent and in a suitable solvent such as dimethylformamide, N-methylpyrrolidone (NMP) or dimethyl sulphoxide (DMSO).

In the case where the cationic group contains two amine functions which are not chemically differentiated (e.g. linear diamine), it may be introduced in a form in which one of the two functions is protected. A final step of cleaving the protective group is then added.

The polymerization chemistry and the group coupling reactions are conventional and well known to those skilled in the art (see, for example, the patents or patent applications by the applicant, mentioned above).

Association of the POM with an Active Ingredient

The techniques for associating one or more active ingredients with the POM polymers according to the invention are similar to those described in particular in patent U.S. Pat. No. 6,630,171.

The active ingredients may associate spontaneously with the POM polymer as described above.

This association is purely physical and does not involve the creation of a covalent bond between the active ingredient and the polymer.

No step for chemical crosslinking of the particles obtained is envisaged. The absence of chemical crosslinking makes it possible to avoid the chemical degradation of the active ingredient during the crosslinking step for crosslinking the particles containing the active ingredient. Such chemical crosslinking is in fact generally carried out by activation of polymerizable entities and involves potentially denaturing agents such as UV radiation or glutaraldehyde.

The association, according to the invention, of the active ingredient and of the POM polymer may in particular be carried out according to the following methods.

In a first method, the active ingredient is dissolved in an aqueous solution and mixed with an aqueous suspension of the POM polymer.

In a second method, the active ingredient in powdered form is dispersed in an aqueous suspension of the POM polymer and the whole is stirred until a homogeneous clear suspension is obtained.

In a third method, the POM polymer is introduced in powdered form into an aqueous dispersion or solution of the active ingredient.

In a fourth method, the active ingredient and/or the polymer is/are dissolved in a solution containing a water-miscible organic solvent such as ethanol or isopropanol. The procedure is then carried out according to methods 1 to 3 above. Optionally, this solvent may be removed by dialysis or any other technique known to those skilled in the art.

For all these methods, it may be advantageous to facilitate the interaction between the active ingredient and the POM polymer by means of ultrasound or an increase in temperature.

For obvious reasons, the active ingredient/POM polymer weight ratio is capable of varying significantly as a function of the dose of active ingredient considered.

More particularly, this ratio may range between 0.1% and 300% by weight, between 1% and 100% by weight, or between 5% and 80% by weight.

Microparticles

According to one particular embodiment, the nanoparticles associated noncovalently with said active ingredient may be used in a composition according to the invention, in the form of microparticles.

According to a first embodiment, these microparticles may be obtained by agglomeration of nanoparticles of the invention according to the methods known to those skilled in the art, for example, by way of nonlimiting illustration, by flocculation, atomization, lyophilization, or coacervation.

According to another embodiment, the microparticles have a core containing said nanoparticles and at least one coating layer conditioning a release profile, for said active ingredient, which is regulated as a function of pH, said coating layer being formed by a material comprising at least one polymer A having a solubilization pH value within the pH range of 5 to 7, associated with at least one hydrophobic compound B.

The controlled release, as a function of pH, of the nanoparticles from the microparticles is provided by the coating surrounding the core of each reservoir particle. This coating is designed so as to release the active ingredient and the POM polymer at very specific sites of the gastrointestinal tract corresponding, for example, to the windows of absorption of the active ingredient in the gastrointestinal tract.

By virtue of the nature of this coating, the microparticles considered according to the present invention may thus advantageously have a double mechanism of release as a function of time and of pH.

By this expression is meant that they have the following two specificities. Below the solubilization pH value of the polymer A forming the coating of these microparticles, they release only a very limited amount of nanoparticles. On the other hand, when they are present in the intestine or a comparable environment, they provide an effective release of the nanoparticles. This release can then be carried out advantageously in less than 24 hours, in particular in less than 12 hours, especially in less than 6 hours, in particular less than 2 hours, or even in less than 1 hour.

In the case of active ingredients having a very narrow absorption window, for example limited to the duodenum or to the Peyer's patches, the nanoparticles release time is less than 2 hours, and preferably less than 1 hour.

Thus, a composition according to the invention is suitable for releasing, in a first step, the active ingredient associated with the nanoparticles of POM polymer(s) and then dissociating, in a second step, the active ingredient from said nanoparticles.

The size of the microparticles considered according to this variant of the invention is advantageously less than 2,000 µm, in particular ranges from 100 to 1,000 µm, in particular from 100 to 800 µm, and especially from 100 to 500 µm.

For the purpose of the invention, the particle size is expressed as volume-average diameter $D_{4,3}$ measured by laser particle sizing using a Mastersizer 2000 machine from Malvern Instrument, equipped with the Sirocco 2000 dry process module.

According to this variant embodiment, the coating of the nanoparticles may be formed by a composite material obtained by mixing:
 at least one compound A having a solubilization pH value within the pH range of 5 to 7;
 at least one hydrophobic compound B;
 and, optionally, at least one plasticizer and/or other conventional excipients.

Polymer A

For the purpose of the present invention, the solubilization pH value of the polymer A is a pH value of the physiological medium or of the model in vitro medium below which the polymer is in an insoluble state and above which this same polymer A is in a soluble state.

For obvious reasons, this pH value is specific to a given polymer and directly linked to its intrinsic physicochemical characteristics, such as its chemical nature and its chain length.

By way of nonlimiting illustration of the polymers A suitable for the invention, mention may in particular be made of:
 copolymer(s) of methacrylic acid and methyl methacrylate,
 copolymer(s) of methacrylic acid and ethyl acrylate,
 cellulosic derivatives such as:
  cellulose acetate phthalate (CAP),
  cellulose acetate succinate (CAS),
  cellulose acetate trimellitate (CAT),
  hydroxypropylmethylcellulose phthalate (or hypromellose phthalate) (HPMCP),
  hydroxypropylmethylcellulose acetate succinate (or hypromellose acetate succinate) (HPMCAS),
 shellac gum,
 polyvinyl acetate phthalate (PVAP),
 and mixtures thereof.

According to one preferred embodiment of the invention, this polymer A is chosen from copolymer(s) of methacrylic acid and methyl methacrylate, copolymer(s) of methacrylic acid and of ethyl acrylate, and mixtures thereof.

As specified above, the polymer A considered according to the invention has a different solubility profile depending on whether it is confronted with a pH value above or below its solubilization pH value.

For the purpose of the invention, the polymer A is generally insoluble at a pH value below its solubilization pH value and, on the other hand, soluble at a pH value above its solubilization pH value.

For example, it may be a polymer of which the solubilization pH value is:
 5.0 like, for example, hydroxypropylmethylcellulose phthalate, and in particular that sold under the name HP-50 by Shin-Etsu,
 5.5 like, for example, hydroxypropylmethylcellulose phthalate, and in particular that sold under the name HP-55 by Shin-Etsu, or the 1:1 copolymer of methacrylic acid and ethyl acrylate, and in particular that sold under the name Eudragit L100-55 from Evonik,
 6.0 like, for example, a 1:1 copolymer of methacrylic acid and methyl methacrylate, and in particular that sold under the name Eudragit L100 from Evonik,
 7.0, for instance a 1:2 copolymer of methacrylic acid and methyl methacrylate, and in particular that sold under the name Eudragit S100 from Evonik.

All these polymers are soluble at a pH value above their solubilization pH.

The coating is advantageously composed of from 25% to 90%, in particular from 30% to 80%, especially from 35% to 70%, or even from 40% to 60% by weight of polymer(s) A relative to its total weight.

More preferably, the polymer A is a 1:1 copolymer of methacrylic acid and ethyl acrylate.

Hydrophobic Compound B

According to a first variant, the compound B may be selected from products that are crystalline in the solid state and that have a melting temperature $T_{mb} \geq 40°$ C., preferably $T_{mb} \geq 50°$ C., and even more preferably $40°$ C.$\leq T_{mb} \leq 90°$ C.

More preferably, this compound is then chosen from the following group of products:
 vegetable waxes alone or as a mixture with one another, such as those sold under the trade marks Dynasan P60; Dynasan 116, among others;
 hydrogenated vegetable oils alone or as a mixture with one another; preferably chosen from the group comprising: hydrogenated cotton oil, hydrogenated soya oil, hydrogenated palm oil, and mixtures thereof;
 mono- and/or di- and/or triesters of glycerol and of at least one fatty acid, preferably behenic acid, alone or as a mixture with one another;
 and mixtures thereof.

According to this embodiment, the B/A weight ratio may range between 0.2 and 1.5, and preferably between 0.45 and 1.

More preferably, the compound B is hydrogenated cotton oil.

Microparticles formed by such a coating are in particular described in document WO 03/30878.

According to a second variant, the compound B may be a polymer that is insoluble in the liquids of the digestive tract.

This polymer that is insoluble in the liquids of the digestive tract or also the gastrointestinal fluids is particularly selected from:
- water-insoluble derivatives of cellulose,
- water-insoluble derivatives of (meth)acrylic (co)polymers,
- and mixtures thereof.

More preferably, it may be chosen from ethylcellulose, and/or derivatives, for example those sold under the name Ethocel®, cellulose acetate butyrate, cellulose acetate, ammonio (meth)acrylate copolymers (copolymer of ethyl acrylate, methyl methacrylate and trimethylammonioethyl methacrylate) type "A" or type "B", in particular those sold under the names Eudragit® RL and Eudragit® RS, poly (meth)acrylic acid esters, in particular those sold under the name Eudragit® NE, and mixtures thereof Quite particularly suitable for the invention are ethylcellulose, cellulose acetate butyrate, and ammonio (meth)acrylate copolymers, in particular those sold under the name Eudragit RS® and Eudragit RL®.

The coating of the microparticles then contains from 10% to 75%, and may preferably contain from 15% to 60%, more preferably from 20% to 55%, or even from 25% to 55% by weight, and even more particularly from 30% to 50%, of polymer(s) A relative to its total weight.

Advantageously, the coating may then be formed, according to this embodiment, from a mixture of the two categories of polymers A and B in a polymer(s) B/polymer(s) A weight ratio greater than 0.25, in particular greater than or equal to 0.3, in particular greater than or equal to 0.4, especially greater than or equal to 0.5, or even greater than or equal to 0.75.

According to another variant embodiment, the polymer(s) A/polymer(s) B ratio is also less than 8, especially less than 4, or even less than 2, and more particularly less than 1.5.

By way of representation of the mixtures of polymers A and B quite particularly suitable for the invention, mention may in particular be made of mixtures of ethylcellulose, of cellulose acetate butyrate or of ammonio (meth)acrylate copolymer type A or B with at least one copolymer of methacrylic acid and ethyl acrylate or one copolymer of methacrylic acid and methyl methacrylate or a mixture thereof.

In addition to the two types of compounds A and B mentioned above, the coating of the nanoparticles according to the invention may comprise at least one plasticizer.

Plasticizer

This plasticizer may in particular be chosen from:
- glycerol and esters thereof, and preferably from acetylated glycerides, glyceryl monostearate, glyceryl triacetate and glyceryl tributyrate,
- phthalates, and preferably from dibutyl phthalate, diethyl phthalate, dimethyl phthalate and dioctyl phthalate,
- citrates, and preferably from acetyl tributyl citrate, acetyl triethyl citrate, tributyl citrate and triethyl citrate,
- sebacates, and preferably from diethyl sebacate and dibutyl sebacate,
- adipates,
- azelates,
- benzoates,
- chlorobutanol,
- polyethylene glycols,
- vegetable oils,
- fumarates, preferably diethyl fumarate,
- malates, preferably diethyl malate,
- oxalates, preferably diethyl oxalate,
- succinates, preferably dibutyl succinate,
- butyrates,
- cetyl alcohol esters,
- malonates, preferably diethyl malonate,
- castor oil,
- and mixtures thereof.

In particular, the coating may comprise less than 30% by weight, preferably from 1% to 25% by weight, and even more preferably from 5% to 20% by weight of plasticizer(s) relative to its total weight.

The formation of the microparticles according to this variant of the invention may be carried out by any conventional technique suitable for the formation of a reservoir capsule, the core of which is formed entirely or partly of at least one active ingredient noncovalently associated with nanoparticles of POM polymer, in particular as defined above.

Preferably, the microparticles are formed by spraying of the compounds A and B and, if present, the other ingredients, including the plasticizer(s), generally in the form of solutes. This solvent medium generally contains organic solvents which may or may not be mixed with water. The coating thus formed is found to be homogeneous in terms of composition, as opposed to a coating formed from a dispersion of these same polymers, in a predominantly aqueous liquid.

According to one preferred variant embodiment, the sprayed solution contains less than 40% by weight of water, in particular less than 30% by weight of water, and more particularly less than 25% by weight of water.

According to another variant embodiment, the nanoparticles noncovalently associated with the active ingredient may be used in a supported form, of microparticle type, in particular on a neutral substrate by means of one or more binders and with one or more conventional excipients.

These microparticles, present in a supported form, may be subsequently coated with one or more layers of coating, as described above.

In the case where it is desired to deposit the AI/POM mixture on a neutral substrate of neutral sphere type, the process may be carried out in the following way:

A conventional binder is added to the homogeneous mixture of active ingredient and of POM, said binder being intended to provide the cohesion of the layer deposited on the neutral core.

Such binders are in particular proposed in Khankari R. K. et al., *Binders and Solvents* in Handbook of Pharmaceutical Granulation Technology, Dilip M. Parikh ed., Marcel Dekker Inc., New York, 1997.

The following are quite particularly suitable for the invention, as binders: hydroxypropylcellulose (HPC), polyvinylpyrrolidone (PVP), methylcellulose (MC) and hydroxypropylmethylcellulose (HPMC).

The depositing of the corresponding mixture is then carried out by conventional techniques known to those skilled in the art. This may in particular involve spraying the colloidal suspension of the active ingredient-loaded nanoparticles containing the binder and, optionally, other compounds onto the support in a fluidized air bed.

Without this being limiting, a composition according to the invention may, for example, contain, in addition to the nanoparticles associated with the active ingredient and the conventional excipients, sucrose and/or dextrose and/or lactose, or alternatively a microparticle of an inert substrate such as cellulose acting as a support for said nanoparticles.

Thus, in a first preferred embodiment of this variant, a composition according to the invention may comprise granules containing the POM, the active ingredient, one or more binders providing the cohesion of the granule and various excipients known to those skilled in the art.

A coating may then be deposited onto this granule by any technique known to those skilled in the art, and advantageously by spray coating, resulting in the formation of microparticles as described above.

The weight composition of a microparticle in accordance with this embodiment is the following:
- the content, by weight, of active ingredient-loaded nanoparticles in the core is comprised between 0.1% and 80%, preferably between 2% and 70%, more preferably between 10% and 60%;
- the content, by weight, of binder in the core is comprised between 0.5% and 40%, preferably between 2% and 25%;
- the content, by weight, of the coating in the microparticle is comprised between 5% and 50%, preferably between 15% and 35%.

In a second preferred embodiment of this variant, a composition according to the invention may comprise neutral cores around which has been deposited a layer containing the active ingredient, the POM nanoparticles, a binder providing the cohesion of this layer and, optionally, various excipients known to those skilled in the art, for example sucrose, trehalose and mannitol. The neutral core may be a particle of cellulose or sugar or any organic or saline inert compound which lends itself to the coating.

The neutral cores thus covered can then be coated with at least one coating layer so as to form microparticles as described above.

The weight composition of a particle according to this embodiment is then the following:
- the content, by weight, of active ingredient-loaded nanoparticles in the core is comprised between 0.1% and 80%, preferably between 2% and 70%, more preferably between 10% and 60%;
- the content, by weight, of neutral core in the core of the microparticles is comprised between 5% and 50%, preferably between 10% and 30%;
- the content, by weight, of binder in the core of the microparticles is comprised between 0.5% and 40%, preferably between 2% and 25%;
- the content, by weight, of the coating in the microparticle is comprised between 5% and 50%, preferably between 15% and 35%.

The present invention relates, in addition, to the novel pharmaceutical, plant-protection, dietary, cosmetic or dietetic preparations produced from the compositions according to the invention.

The composition according to the invention may thus be in the form of a powder, a suspension, a tablet or a gelatin capsule.

The composition according to the invention may in particular be for use in the preparation of medicaments.

According to one variant embodiment, a composition according to the invention may comprise at least two types of nanoparticles, which differ from one another by virtue of the nature of the active ingredient and/or of the POM associated with said active ingredient.

According to yet another variant, which can be combined with the preceding variant, in the case where the nanoparticles are used in the form of microparticles, as described above, a composition according to the invention may combine at least two types of microparticles which differ from one another by virtue of the nature of their coating layer and/or of the active ingredient that they incorporate.

The invention will be explained more clearly by means of the examples hereinafter, given only by way of illustration.

EXAMPLES

Example 1

Preparation of a Solution of Paclitaxel in an Aqueous Buffer (Reference)

0.49 mg of paclitaxel (Bioxel) is introduced into a 2 liter volumetric flask. The flask is topped up to the fill line with a 0.05 M phosphate buffer at pH 7.0. The preparation is stirred using a magnetic bar, at 37° C. After magnetic stirring for 2.5 h at 37° C., a few grains of undissolved powder remain.

The preparation is then placed in an ultrasonic bath for 60 min at ambient temperature. A few grains of powder are still undissolved after ultrasonic treatment.

The solubility of paclitaxel in an aqueous buffer at pH 7.0 is less than 0.25 µg/ml, i.e. less than 0.3 µmol/l.

Example 2

Preparation of Aqueous Formulations of Paclitaxel with a Sodium Polyglutamate with a Degree of Polymerization DP=100 and 20%-grafted with Vitamin E, at a Polymer Concentration of 20 mg/ml Formulation 1

4.99 mg of paclitaxel (Bioxel) are introduced into a pill-box. 10 ml of aqueous solution of polyglutamate with a DP=100, 20%-grafted with vitamin E, at pH 7.0 and at a concentration of 20 mg/ml, are added. The preparation is placed in an ultrasonic bath at ambient temperature for 90 minutes. After ultrasonic treatment, a completely clear solution is obtained.

Formulation 2

10.33 mg of paclitaxel (Bioxel) are introduced into a pill-box. 10 ml of aqueous solution of polyglutamate polymer with a DP=100, 20%-grafted with vitamin E, at pH 7.0 and at a concentration of 20 mg/ml, are added. The preparation is placed in an ultrasonic bath at ambient temperature for 2.5 h. After ultrasonic treatment, a few grains of paclitaxel powder have not dissolved.

Formulation 3

7 mg of paclitaxel (Bioxel) are introduced into a pill-box. 10 ml of aqueous solution of polyglutamate polymer 20%-grafted with vitamin E, at pH=7.0 and at a concentration of 20 mg/ml, are added. The preparation is placed in an ultrasonic bath at ambient temperature for 2.5 h. After ultrasonic treatment, a completely clear solution is obtained.

The solubility of paclitaxel in an aqueous solution containing 20 mg/ml of polyglutamate with a DP=100, 20%-grafted with vitamin E is around 0.8 mg/ml, i.e. 47 µmol of paclitaxel per gram of POM polymer.

The solubility of paclitaxel is thus considerably improved by the use of the POM polymer nanoparticles described above.

Example 3

Preparation of Aqueous Formulations of Paclitaxel with a Sodium Polyglutamate with a DP=100 and 20%-grafted with Vitamin E, at a Polymer Concentration of 90 mg/ml Formulation 1

21.21 mg of paclitaxel (Bioxel) are introduced into a pill-box. 10 ml of aqueous solution of polyglutamate polymer with a DP=100, 20%-grafted with vitamin E, at pH=7.0 and at a concentration of 90 mg/ml, are added. The preparation is placed in an ultrasonic bath at ambient temperature for 60 min. After ultrasonic treatment, a completely clear solution is obtained. All the paclitaxel powder is solubilized.

Formulation 2

39.68 mg of paclitaxel (Bioxel) are introduced into a pill-box. 10 ml of aqueous solution of polyglutamate polymer with a DP=100, 20%-grafted with vitamin E, at pH=7.0 and at a concentration of 90 mg/ml, are added. The preparation is placed in an ultrasonic bath at ambient temperature for 5 h. After ultrasonic treatment, a few grains of paclitaxel powder have not dissolved.

Formulation 3

35.05 mg of paclitaxel (Bioxel) are introduced into a pill-box. 10 ml of aqueous solution of polyglutamate polymer 20%-grafted with vitamin E, at pH=7.0 and at a concentration of 90 mg/ml, are added. The preparation is placed in an ultrasonic bath at ambient temperature for 5 h. After ultrasonic treatment, a few grains of paclitaxel powder have not dissolved.

The solubility of paclitaxel in an aqueous solution containing 90 mg/ml of polyglutamate 20%-grafted with vitamin E is comprised between 3.5 mg/ml and 4 mg/ml, i.e. 49 µmol of paclitaxel per gram of POM polymer.

Example 4

Preparation of Aqueous Formulations of Paclitaxel Solubilized by Different POM Polymers (Formulations Containing 20 g/l Polymer)

In this example the POM polymers used are sodium polyglutamates having a DP=100 and variable vitamin E grafting rates.

Preparation of the formulations is based on the protocol described in Example 2. The solubility value is estimated by a successive approach by attempting to dissolve 5 to 10 mg of paclitaxel in 10 ml of aqueous solution of POM polymer at pH 7.0 and with a polymer concentration of 20 mg/ml. The preparation is placed in an ultrasonic bath at ambient temperature for 90 minutes. The preparation is then left under stirring at ambient temperature overnight. The appearance of the solution is then visually checked in order to see if the paclitaxel powder introduced is entirely solubilized or if residual paclitaxel crystals remain.

TABLE 1

Solubilization of paclitaxel in an aqueous solution containing 20 g/l of sodium polyglutamate with a DP = 100, 5%-20%-grafted with vitamin E (VE), at pH = 7.0 at ambient temperature.

| % VE on polymer | Total concentration of active ingredient solibilized for 20 g/l of polymer (mol/l) | Solubilized active ingredient in µmol per g of polymer |
|---|---|---|
| 5 | $2.3 \cdot 10^{-4}$ | 12 |
| 10 | $5.9 \cdot 10^{-4}$ | 29 |
| 15 | $9.4 \cdot 10^{-4}$ | 47 |
| 20 | $9.4 \cdot 10^{-4}$ | 47 |

The solubility of the active ingredient measured without polymer in similar conditions in Example 1 is $3 \cdot 10^{-7}$ mol/l. Table 1 thus shows that the presence of POM polymer at 20 g/l allows the solubility of paclitaxel to be increased by a factor of 500 to 3,000 according to the polymer.

Table 1 clearly shows that for a polymer with a DP=100 a maximum solubilizing power is obtained for polymers having between 15% and 20% vitamin E and thus it is for these polymers that the largest quantity of solubilized active ingredient is observed.

Example 5

Preparation of Aqueous Formulations of Paclitaxel Solubilized by Different POM Polymers (Formulations Containing High Polymer Concentrations)

In this example the POM polymers used are sodium polyglutamates with a degree of polymerization DP=100 and variable vitamin E grafting rates. The POM polymer solution is used at a high concentration in order to solubilize as much active ingredient as possible. However, in order that the solution can be easily handled, the viscosity of the solution is maintained at <100 mPa·s (at 20° C.) which thus limits the polymer concentration in a different manner according to the polymers.

Preparation of the formulations is based on the protocol described in Example 3. The solubility value is estimated by the successive approach by attempting to dissolve 5 to 15 mg of paclitaxel in 2 ml of concentrated aqueous solution of POM polymer at pH 7.0. The preparation is placed in an ultrasonic bath at ambient temperature for 90 minutes. If insoluble matter remains visible to the naked eye, the solution is replaced in the ultrasonic bath for a further 90 minutes. The preparation is then stirred at ambient temperature overnight. The appearance of the solution is then visually checked in order to see if the paclitaxel powder introduced is completely solubilized or if residual paclitaxel crystals remain.

TABLE 2

Solubilization of paclitaxel by a concentrated aqueous solution of sodium polyglutamate with DP = 100, 5% to 30%-grafted with vitamin E (VE), at pH = 7.0, at ambient temperature

| % VE on polymer (%) | Concentration of the polymer solution (mg/ml)) | Total concentration of solubilized active ingredient (mol/l) | Solubilized active ingredient in µmol per g of polymer |
|---|---|---|---|
| 10 | 52.8 | $1.5 \cdot 10^{-3}$ | 29 |
| 15 | 84.6 | $3.5 \cdot 10^{-3}$ | 42 |
| 20 | 156 | $6.4 \cdot 10^{-3}$ | 41 |
| 30 | 53.5 | $<1.4 \cdot 10^{-3}$ | <26 |

Table 2 shows that the polymers with a DP=100 containing between 15% and 20% vitamin E allow the polymer concentration to be substantially increased while maintaining an acceptable viscosity and thus allowing significant concentrations of solubilized active ingredient ($>3 \cdot 10^{-3}$ mol/l) to be obtained. It should be recalled that the solubility of the active ingredient measured without polymer in similar conditions in Example 1 is $3 \cdot 10^{-7}$ mol/l i.e. more than 10,000 times less.

Example 6

Preparation of Aqueous Formulations of Simvastatin and Nifedipine Solubilized by a Sodium Polyglutamate with a DP=100 and 20%-grafted with Vitamin E (Formulations Containing 20 g/l of Polymer)

Proceeding according to the method disclosed in Examples 1 and 2 above, the aqueous solubility of simvastatin and nifedipine were determined, firstly in the absence of POM polymer, then in the presence of polyglutamate with a degree of polymerization of 100, 20%-grafted with vitamin E, at pH 7.0 and concentrated to 20 g/l. The results are summarized in Table 3 below.

TABLE 3

Solubilization of simvastatin and nifedipine with an aqueous solution containing 20 g/l of polyglutamate with a DP = 100, 20%-grafted with vitamin E, at pH = 7, at ambient temperature

| Active agent | Molecular mass M (g/mol) | Solubility (mol/l) | Solubilized active ingredient for 20 g/l polymer (mol/L) | Solubilized active ingredient in µmol per g of polymer |
|---|---|---|---|---|
| Simvastatin | 419 | $1.19 \cdot 10^{-4}$ | $7.64 \cdot 10^{-3}$ | 382 |
| Nifedipine | 346 | $2.89 \cdot 10^{-5}$ | $8.67 \cdot 10^{-4}$ | 43 |

It should be noted that the polyglutamate polymer with a DP of 100, 20%-grafted with vitamin E, dramatically solubilizes the relatively insoluble active ingredients. It should also be noted that even higher solubilities can be obtained with higher concentrations of POM polymer.

Example 7

Preparation of Aqueous Formulations of Carvedilol Base Solubilized by Different POM Polymers (Formulations Containing 20 g/l of Polymer)

In this example the POM polymers used are sodium polyglutamates with a degree of polymerization comprised between 25 and 100 and variable vitamin E grafting rates. Polymers the glutamates of which are partly modified with arginine (cationic groups) and ethanolamine (neutral groups) are also tested.

40 to 50 mg of carvedilol base are introduced into a 15 ml Falcon tube. 5 ml of aqueous solution of concentrated POM polymer at 20 mg/ml and at pH 7.0 are added. The preparation is placed in an ultrasonic bath at ambient temperature for 90 minutes. After this stage, the preparation is centrifuged at 9,000 rpm for 30 minutes in order to eliminate any undissolved crystals. In all cases, the supernatant is perfectly clear. It is diluted 1,000 times with a phosphate buffer at pH 7.0. The concentration of solubilized carvedilol is determined by UV spectrometry (at a wavelength of 240 nm and using a cell with a 1 cm optical path).

TABLE 4

Solubilization of carvedilol base with an aqueous solution containing 20 g/l of sodium polyglutamate with a DP = 100, 2 to 20%-grafted with vitamin E (VE), at pH = 7.0 at ambient temperature.

| % VE on polymer (%) | Total concentration of the solubilized active ingredient for 20 g/l of polymer (mol/l) | Solubilized active ingredient in µmol per g of polymer |
|---|---|---|
| 2 | $2.95 \cdot 10^{-3}$ | 148 |
| 5 | $6.64 \cdot 10^{-3}$ | 332 |
| 10 | $1.53 \cdot 10^{-2}$ | 763 |
| 20 | $1.53 \cdot 10^{-2}$ | 763 |

TABLE 5

Solubilization of carvedilol base with an aqueous solution containing 20 g/l of sodium polyglutamate with a DP ranging from 25 to 100, 10%-grafted with vitamin E, at pH = 7.0 at ambient temperature.

| Degree of polymerization of the polymer | Total concentration of solubilized active ingredient for 20 g/l of polymer (mol/l) | Solubilized active ingredient in µmol per g of polymer |
|---|---|---|
| 25 | $1.48 \cdot 10^{-2}$ | 738 |
| 50 | $1.53 \cdot 10^{-2}$ | 677 |
| 100 | $1.53 \cdot 10^{-2}$ | 763 |

TABLE 6

Solubilization of carvedilol base with an aqueous solution containing 20 g/l of sodium polyglutamate with a DP = 50, 10%-grafted with vitamin E, with cationic (arginine) and optionally neutral (ethanolamine) grafts at pH = 7.0 at ambient temperature.

| % arginine | % ethanolamine | Total concentration of solubilized active ingredient for 20 g/l of polymer (mol/l) | Solubilized active ingredient in µmol per g of polymer |
|---|---|---|---|
| 40 | 45 | $1.72 \cdot 10^{-3}$ | 86 |
| 60 | 0 | $9.35 \cdot 10^{-3}$ | 467 |

The same experiment is carried out in the absence of polymer and it is found that the solubility of carvedilol base at pH 7 is $1.2 \cdot 10^{-4}$ mol/l.

In the presence of 20 mg/ml of POM polymer, the solubility of carvedilol base is thus increased by a factor of approximately 10 to 100 depending on the polymers. Table 4 further shows that for sodium polyglutamates with a DP=100 grafted with vitamin E, the maximum solubilization is obtained for polyglutamates 10 to 20%-grafted with vitamin E.

Example 8

Preparation of Aqueous Formulations of Carvedilol Base Solubilized with Different POM Polymers (Formulations Containing High Polymer Concentrations)

In this example the POM polymers used are sodium polyglutamates with a degree of polymerization DP=100 and variable vitamin E grafting rates. The POM polymer solution is used at a high concentration in order to solubilize as much active ingredient as possible. However, in order to ensure that the solution can be handled easily, the solution is maintained at a viscosity <100 mPa·s (at 20° C.), which thus limits the polymer concentration in a different manner according to the polymers.

50 to 100 mg of carvedilol base is introduced into a pill-box. 2 ml of concentrated aqueous solution of POM polymer at pH 7 is added. The preparation is placed in an ultrasonic bath at ambient temperature for 90 minutes. If insoluble matter remains which is visible to the naked eye, the solution is replaced in the ultrasonic bath for a further 90 minutes. The formulation is then stirred at ambient temperature overnight. As in the previous example, the formulation is then centrifuged and the supernatant is analyzed by HPLC.

TABLE 7

Solubilization of carvedilol base with a concentrated aqueous solution of sodium polyglutamate with a DP = 100, 10 to 20%-grafted with vitamin E (VE) at pH = 7.0 at ambient temperature.

| % VE on polymer (%) | Concentration of the polymer solution (mg/ml) | Total concentration of solubilized active ingredient (mol/l) | Solubilized active ingredient in µmol per g of polymer |
|---|---|---|---|
| 10 | 52.8 | $3.37 \cdot 10^{-2}$ | 638 |
| 15 | 84.6 | $4.01 \cdot 10^{-2}$ | 474 |
| 20 | 156 | $8.46 \cdot 10^{-2}$ | 543 |

Table 7 shows that the total concentration of active ingredient solubilized in the presence of POM polymers in concentrated solution is significantly greater that the solubility of carvedilol base in pure water at the same pH ($1.2 \cdot 10^{-4}$ mol/l). The solubility is thus increased by a factor comprised between 100 and 1,000.

Example 9

Preparation of Aqueous Formulations of Ketoconazole Solubilized with Different POM Polymers (Formulations Containing 20 g/l of Polymer)

In this example the POM polymers used are sodium polyglutamates with a degree of polymerization of 100 and variable vitamin E grafting rates. A polymer the glutamates of which are partly modified by arginine (cationic groups) is also tested.

2 to 40 mg of ketoconazole powder is introduced into a 15 ml Falcon tube. 10 ml of aqueous solution of POM polymer at pH 7.0 and concentrated at 20 mg/ml is added. The preparation is placed in an ultrasonic bath at ambient temperature for 90 minutes. The preparation is then stirred at ambient temperature overnight. The appearance of the solution is then checked visually in order to see if the ketoconazole powder introduced is completely solubilized or if residual ketoconazole crystals remain.

TABLE 8

Solubilization of ketoconazole with an aqueous solution containing 20 g/l of sodium polyglutamate with a DP = 100, 2 to 20%-grafted with vitamin E (VE), at pH = 7.0, at ambient temperature

| % VE on polymer (%) | Total concentration of solubilized active ingredient for 20 g/l of polymer (mol/l) | Solubilized active ingredient in µmol per g of polymer |
|---|---|---|
| 2 | $5.65 \cdot 10^{-4}$ | 28 |
| 5 | $2.54 \cdot 10^{-3}$ | 127 |
| 10 | $7.16 \cdot 10^{-3}$ | 358 |
| 15 | $7.16 \cdot 10^{-3}$ | 358 |
| 20 | $6.97 \cdot 10^{-3}$ | 348 |

Table 8 shows clearly that maximum solubilization is obtained for the polymers which are 10 to 20%-grafted with vitamin E.

The same tests were carried out with a cationic polymer.

TABLE 9

Solubilization of carvedilol with an aqueous solution containing 20 g/l of sodium polyglutamate with a DP = 50, 10%-grafted with vitamin E with cationic grafts (arginine) at pH = 7.0, at ambient temperature

| arginine (%) | Total concentration of solubilized active ingredient for 20 g/l of polymer (mol/l) | Solubilized active ingredient in µmol per g of polymer |
|---|---|---|
| 60 | $5.65 \cdot 10^{-4}$ | 28 |

The same experiment is carried out in the absence of polymer and it is found that the solubility of ketoconazole at pH 7.0 is approximately $2 \cdot 10^{-5}$ mol/l.

In the presence of 20 mg/ml of POM polymer, the solubility of ketoconazole is thus increased by a factor comprised between 25 and 400 depending on the polymers.

Example 10

Preparation of Aqueous Formulations of Ketoconazole Solubilized with Different POM Polymers (Formulations Containing High Polymer Concentrations)

In this example, the POM polymers used are sodium polyglutamates with a degree of polymerization DP=100 and variable vitamin E grafting rates. The solution of POM polymer is used at a high concentration so as to solubilize as much active ingredient as possible. However, in order that the solution can be easily handled, the viscosity of the solution is maintained <100 mPa·s (at 20° C.) which thus limits the polymer concentration in a different manner according to the polymer.

10 to 60 mg of ketoconazole powder is introduced into a glass pill-box, 2 ml of concentrated aqueous solutions of POM polymer at pH 7.0 is added. The preparation is placed in an ultrasonic bath at ambient temperature for 90 minutes. If insoluble matter visible to the naked eye remains, the solution is replaced in the ultrasonic bath for a further 90 minutes. The preparation is then stirred at ambient temperature overnight. The appearance of the solution is then visually checked in order to see if the ketoconazole powder introduced is completely solubilized or if residual ketoconazole crystals remain.

TABLE 10

Solubilization of ketoconazole with a concentrated aqueous solution of sodium polyglutamate with a DP = 100, 2 to 30%-grafted with vitamin E (VE) at pH = 7.0 at ambient temperature

| % VE on polymer (%) | Concentration of the polymer solution (mg/ml) | Total concentration of solubilized active ingredient (mol/l) | Solubilized active ingredient in µmol per g of polymer |
|---|---|---|---|
| 10 | 52.8 | $1.60 \cdot 10^{-2}$ | 303 |
| 15 | 84.6 | $3.11 \cdot 10^{-2}$ | 367 |
| 20 | 156 | $5.35 \cdot 10^{-2}$ | 343 |
| 30 | 53.5 | $1.41 \cdot 10^{-2}$ | 264 |

Table 10 shows that the polymers with a DP=100 containing between 15% and 20% vitamin E allow the polymer concentration to be substantially increased while maintaining an acceptable viscosity and thus allowing significant concentrations of solubilized active ingredient ($>3 \cdot 10^{-2}$ mol/l) to be obtained. It is recalled that the solubility of the active ingredient measured without polymer in similar conditions as in the previous example is $2 \cdot 10^{-5}$ mol/l i.e. more than 1,000 times less.

Example 11

Preparation of Aqueous Formulations of Cyclosporin-A Solubilized with Different POM Polymers (Formulations Containing 20 g/l of Polymer).

In this example the POM polymers used are sodium polyglutamates having a degree of polymerization comprised between 25 and 100 and variable vitamin E grafting rates.

40 to 50 mg of cyclosporin-A is introduced into a 15 ml Falcon tube. 5 ml aqueous solution of POM polymer at pH 7 and concentrated at 20 mg/ml is added. The preparation is placed in an ultrasonic bath at ambient temperature for 90 minutes. The preparation is then stirred at ambient temperature overnight. The preparation is centrifuged at 9,000 rpm for 30 minutes. The supernatant is measured by HPLC in order to determine the concentration of cyclosporin-A in the aqueous solution.

TABLE 11

Solubilization of cyclosporin-A with an aqueous solution containing 20 g/l of sodium polyglutamate with a DP = 100, 5 to 30%-grafted with vitamin E (VE) at pH = 7.0, at ambient temperature

| % VE on polymer (%) | Total concentration of solubilized active ingredient for 20 g/l of polymer (mol/l) | Solubilized active ingredient in μmol per g of polymer |
|---|---|---|
| 5 | $4.46 \cdot 10^{-3}$ | 223 |
| 10 | $6.24 \cdot 10^{-3}$ | 312 |
| 15 | $6.49 \cdot 10^{-3}$ | 324 |
| 20 | $5.78 \cdot 10^{-3}$ | 289 |
| 30 | $4.03 \cdot 10^{-3}$ | 202 |

TABLE 12

Solubilization of cyclosporin-A with an aqueous solution containing 20 g/l of sodium polyglutamate with a DP between 25 and 100, 10%-grafted with vitamin E at pH = 7.0 at ambient temperature

| Degree of polymerization of the polymer | Total concentration of solubilized active ingredient for 20 g/l of polymer (mol/l) | Solubilized active ingredient in μmol per g of polymer |
|---|---|---|
| 25 | $5.86 \cdot 10^{-3}$ | 293 |
| 50 | $6.16 \cdot 10^{-3}$ | 308 |
| 100 | $6.24 \cdot 10^{-3}$ | 312 |

The same experiment was carried out in the absence of polymer and it was found that the solubility of cyclosporin-A at pH 7 is approximately $2.5 \cdot 10^{-5}$ mol/l In the presence of 20 mg/ml of POM polymer, the solubility of ketoconazole is thus increased by a factor of approximately 200. Table 11 further shows that for sodium polyglutamates with a DP=100 grafted with vitamin E, the maximum solubilization is obtained for polyglutamates 10 to 20%-grafted with vitamin E Example 12

Preparation of Aqueous Formulations of Cyclosporin-A Solubilized with Different POM Polymers (Formulations Containing High Concentrations of Polymer).

In this example the POM polymers used are sodium polyglutamates with a degree of polymerization of 100 or 25 and variable vitamin E grafting rates. The solution of POM polymer is used at a high concentration in order to solubilize as much active ingredient as possible. However, in order that the solution can be easily handled, the viscosity of the solution is maintained at <100 mPa·s (at 20° C.) which thus limits the polymer concentration in a different manner depending on the polymers.

60 to 100 mg of cyclosporin-A base is introduced into a pill-box. 2 ml of concentrated aqueous solution of POM polymer at pH 7 is added. The preparation is placed in an ultrasonic bath at ambient temperature for 90 minutes. If insoluble matter remains which is visible to the naked eye, the solution is replaced in the ultrasonic bath for a further 90 minutes. The preparation is then stirred at ambient temperature overnight. The preparation is then centrifuged at 9,000 rpm for 30 minutes. The supernatant is measured by HPLC in order to determine the cyclosporin-A concentration in the aqueous solution.

TABLE 13

Solubilization of cyclosporin-A with a concentrated aqueous solution of sodium polyglutamate with a DP = 100, 10 to 20%-grafted with vitamin E (VE) at pH = 7.0 at ambient temperature.

| % VE on polymer (%) | Concentration of the polymer solution (mg/ml) | Total concentration of solubilized active ingredient (mol/l) | Solubilized active ingredient in μmol per g of polymer |
|---|---|---|---|
| 10 | 52.8 | $4.80 \cdot 10^{-2}$ | 910 |
| 15 | 84.6 | $7.85 \cdot 10^{-2}$ | 928 |
| 20 | 90.0 | $7.89 \cdot 10^{-2}$ | 876 |

TABLE 14

Solubilization of cyclosporin-A with a concentrated aqueous solution of sodium polyglutamate with a DP of 25 or 100, 20%-grafted with vitamin E at pH = 7.0 at ambient temperature.

| Degree of polymerization | Concentration of the polymer solution (mg/ml) | Total concentration of solubilized active ingredient (mol/l) | Solubilized active ingredient in μmol per g of polymer |
|---|---|---|---|
| 100 | 90 | $7.89 \cdot 10^{-2}$ | 876 |
| 25 | 145 | $9.44 \cdot 10^{-2}$ | 651 |

Table 13 shows that the polymers with a DP=100 containing between 15% and 20% vitamin E allow the polymer concentration to be substantially increased while maintaining an acceptable viscosity and thus allowing significant concentrations of solubilized active ingredient ($>2.6 \cdot 10^{-2}$ mol/l) to be obtained. It is recalled that the solubility of the active ingredient measured without polymer in similar conditions in the previous Example is approximately $2.5 \cdot 10^{-5}$ mol/l i.e. more than 1,000 times less.

Example 13

Measurement of the Shear Viscosity (mPa/s) of an Aqueous Solution of POM Polymer at a Concentration of 50 mg/ml with a Velocity Gradient of 10 s$^{-1}$.

All the samples are prepared at 50 mg/ml, either by dilution in pure water of concentrated solutions if the initial concentration after synthesis is >50 mg/ml, or after concentration in a rotary evaporator if the initial concentration of the solution is <50 mg/ml.

The viscosity of aqueous polymer solutions is measured at 20° C. using a Bohlin Gemini model rheometer equipped with a cone-plane type geometry of 4 cm diameter and 1° angle.

TABLE 15

Measurements of viscosity (at 20° C. and for a shear gradient of 10 s$^{-1}$) of solutions at 50 mg/ml of sodium polyglutamates with different DPs 5%-grafted with vitamin E (VE).

|  |  | Viscosity (Mpa · s) |
|---|---|---|
| Degree of polymerization | 25 | <10 |
|  | 50 | <10 |
|  | 100 | 25 |
|  | 220 | >1,000 |

These results show clearly that for vitamin E grafting rates of 5%, a polymer not according to the invention in terms of DP results in a too high viscosity.

The invention claimed is:

1. Composition comprising at least one active ingredient with aqueous solubility less than 1 g/l in pure water, measured at ambient temperature, said active ingredient being present therein in a form noncovalently associated with nanoparticles formed by at least one POM polymer of formula (II) below, or a pharmaceutically acceptable salt thereof:

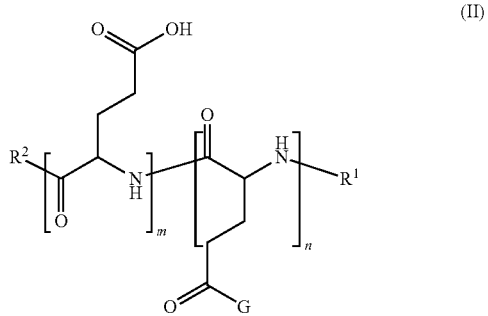

(II)

in which:
R$^1$ is selected from the group consisting of: a hydrogen atom, a linear C$_2$ to C$_{10}$ acyl group, a branched C$_3$ to C$_{10}$ acyl group, a pyroglutamate group and a hydrophobic group G;
R$^2$ is a —NHR$^5$ group or a terminal amino acid residue linked by the nitrogen;
R$^5$ is selected from the group consisting of: a hydrogen atom, a linear C$_1$ to C$_{10}$ alkyl group, a branched C$_3$ to C$_{10}$ alkyl group and a benzyl group;
G is a tocopheryloxy radical;
m and n are positive, non-zero integers;
(m+n) ranges from 25 to 100;
the molar grafting rate of the hydrophobic groups G, (n)/(n+m) ranges from 10 to 21%;
in which said active ingredient is present in a proportion of at least 20 µmol/g of POM,
and wherein the aqueous solubilization of said active ingredient is increased when in said composition.

2. The composition of claim 1, wherein the POM bears at least one graft of polyalkylene glycol type linked to a glutamate unit.

3. The composition of claim 1, wherein the polyalkylene glycol is a polyethylene glycol.

4. The composition of claim 1, wherein the size of the nanoparticles formed by said POM polymer ranges from 1 to 1,000 nm.

5. The composition of claim 1, wherein said active ingredient has a mass of less than 2,000 Da.

6. The composition of claim 1, wherein said active ingredient is a nonpeptide active ingredient.

7. The composition of claim 1, wherein said active ingredient is a molecule of therapeutic, cosmetic, prophylactic or imaging interest.

8. The composition of claim 1, wherein said active ingredient is a therapeutic active ingredient.

9. The composition of claim 1, wherein said composition provides a release profile, for said active ingredient, which is regulated as a function of time.

10. The composition of claim 1, wherein said nanoparticles noncovalently associated with said active ingredient are agglomerated in the form of microparticles.

11. The composition of claim 1, wherein said nanoparticles noncovalently associated with said active ingredient are used in a supported form.

12. The composition of claim 9, wherein said nanoparticles noncovalently associated with said active ingredient are used in the form of microparticles, said microparticles having a core containing said nanoparticles noncovalently associated with said active ingredient and at least one coating layer conditioning a release profile, for said active ingredient, which is also regulated as a function of pH, said coating layer being formed by a composite material comprising at least one polymer A having a solubilization pH value within the pH range of 5 to 7, and at least one hydrophobic compound B.

13. The composition of claim 12, wherein the polymer A is selected from the group consisting of: copolymer(s) of methacrylic acid and methyl methacrylate, copolymer(s) of methacrylic acid and ethyl acrylate, cellulose acetate phthalate, cellulose acetate succinate, cellulose acetate trimellitate, hydroxypropylmethylcellulose phthalate, hydroxypropylmethylcellulose acetate succinate, shellac gum, polyvinyl acetate phthalate, and mixtures thereof.

14. The composition of claim 12, wherein the coating layer contains from 25% to 90% by weight of polymer(s) A relative to its total weight.

15. The composition of claim 12, wherein the hydrophobic compound B is selected from products that are crystalline in the solid state and that have a melting temperature T$_{mb}$ greater than or equal to 40° C.

16. The composition of claim 15, wherein the compound B is selected from the group consisting of: vegetable waxes; hydrogenated vegetable oils taken alone or as a mixture with one another; monoesters glycerol and of at least one fatty acid, diesters of glycerol and of at least one fatty acid, triesters of glycerol and of at least one fatty acid and mixtures thereof.

17. The composition of claim 12, wherein the compound B is a polymer that is insoluble in the gastrointestinal fluids.

18. The composition of claim 17, wherein said polymer B is chosen from: water-insoluble derivatives of cellulose, and water-insoluble derivatives of (meth)acrylic (co)polymers.

19. The composition of claim 10, wherein the size of the microparticles is less than 2,000 µm.

20. The composition of claim 1, wherein said composition comprises at least two types of nanoparticles noncovalently associated with said active ingredient, said nanoparticles differing from one another by virtue of the nature of the active ingredient or of the POM associated with said active ingredient.

21. The composition of claim 12, wherein said composition combines at least two types of microparticles which differ from one another by virtue of the nature of their coating layer or of the active ingredient that they incorporate.

22. The composition of claim 1, wherein said composition is formulated in the form of a powder or a suspension, or in the form of a tablet or a gelatin capsule.

23. The composition of claim 1, wherein said composition is intended for use in the preparation of medicaments.

24. The composition of claim 10, wherein said composition is suitable for releasing, in a first step, the active ingredient associated with the nanoparticles of POM polymer(s) and then dissociating, in a second step, the active ingredient from said nanoparticles.

25. The composition of claim 1, wherein the size of the nanoparticles ranges from 5 to 500 nm.

26. The composition of claim 1, wherein the size of the nanoparticles ranges from 30 to 300 nm.

27. The composition of claim 1, wherein the size of the nanoparticles ranges from 10 to 100 nm.

28. The composition of claim 8, wherein said active ingredient is selected from the group consisting of: paclitaxel, carvedilol base, simvastatin, nifedipine, ketoconazole, and cyclosporin A.

29. The composition of claim 12, wherein the coating layer contains from 30% to 80% by weight of polymer(s) A relative to its total weight.

30. The composition of claim 12, wherein the coating layer contains from 35% to 70% by weight of polymer(s) A relative to its total weight.

31. The composition of claim 12, wherein the coating layer contains from 40% to 60% of polymer(s) A relative to its total weight.

32. The composition of claim 12, wherein the hydrophobic compound B is selected from products that are crystalline in the solid state and that have a melting temperature $T_{mb}$ greater than or equal to 50° C.

33. The composition of claim 12, wherein the hydrophobic compound B is selected from products that are crystalline in the solid state and that have a melting temperature $40° C. \leq T_{mb} \leq 90° C$.

34. The composition of claim 18, wherein said polymer B is a water-insoluble derivatives of cellulose chosen from ethylcellulose, cellulose acetate butyrate and cellulose acetate.

35. The composition of claim 18, wherein said polymer B is a water-insoluble derivatives of (meth)acrylic (co)polymers selected from the group consisting of: ammonio (meth)acrylate copolymers, (co)polymers of ethyl acrylate, methyl methacrylate and trimethylammonioethyl methacrylate, type "A" or type "B", and poly(meth)acrylic acid esters.

36. The composition of claim 10, wherein the size of the microparticles is 100 to 1,000 µm.

37. The composition of claim 36, wherein the size of the microparticles is 100 to 800 µm.

38. The composition of claim 37, wherein the size of the microparticles is 100 to 500 µm.

* * * * *